United States Patent [19]

Burns et al.

[11] Patent Number: 5,137,512
[45] Date of Patent: Aug. 11, 1992

[54] MULTISEGMENT BALLOON PROTECTOR FOR DILATATION CATHETER

[75] Inventors: Matthew M. Burns, Minneapolis; Scott R. Smith, Chaska, both of Minn.

[73] Assignee: SciMed Life Systems, Inc., Maple Grove, Minn.

[21] Appl. No.: 625,795

[22] Filed: Dec. 11, 1990

Related U.S. Application Data

[63] Continuation of Ser. No. 325,453, Mar. 17, 1989, abandoned.

[51] Int. Cl.⁵ .............................. A61M 25/00
[52] U.S. Cl. ..................... 604/96; 604/163; 606/192; 606/191
[58] Field of Search ............... 604/96–103, 604/198, 263, 163; 606/192–195, 191

[56] References Cited

U.S. PATENT DOCUMENTS

| | | | |
|---|---|---|---|
| 2,486,056 | 10/1949 | Oclassen | 604/192 |
| 3,409,016 | 12/1968 | Foley | 604/192 X |
| 3,822,593 | 7/1974 | Oudewaal | 206/306 X |
| 4,147,169 | 4/1979 | Taylor | 604/100 |
| 4,248,246 | 2/1981 | Ikeda | 604/263 X |
| 4,275,591 | 6/1981 | Wand | 206/306 X |
| 4,416,267 | 11/1983 | Garren et al. | 128/1 R |
| 4,449,532 | 5/1984 | Storz | 606/191 |
| 4,573,470 | 3/1986 | Samson et al. | 128/344 |
| 4,592,744 | 6/1986 | Jagger et al. | 604/192 |
| 4,636,201 | 1/1987 | Ambrose et al. | 604/263 X |
| 4,762,125 | 8/1988 | Leiman et al. | 128/207.15 |
| 4,771,776 | 9/1988 | Powell et al. | 128/344 |
| 4,846,344 | 7/1989 | Bala | 206/306 |
| 4,846,801 | 7/1989 | Okuda et al. | 604/263 X |
| 4,921,483 | 5/1990 | Wijay et al. | 604/96 |
| 5,002,558 | 3/1991 | Klein et al. | 606/192 |
| 5,066,298 | 11/1991 | Hess | 606/194 |

Primary Examiner—Robert A. Hafer
Assistant Examiner—Kerry Owens
Attorney, Agent, or Firm—Kinney & Lange

[57] ABSTRACT

A multisegment balloon protector, includes several protectors each of which covers and tightly fits over a portion of the length of a balloon of a dilatation catheter.

30 Claims, 2 Drawing Sheets

MULTISEGMENT BALLOON PROTECTOR FOR DILATATION CATHETER

This is a continuation of application Ser. No. 07/325,454 filed on Mar. 17, 1989, abandoned as of the date of this application.

BACKGROUND OF THE INVENTION

1. Field of the Invention

The invention relates to the field of angioplasty. In particular, the present invention relates to a balloon protector for a dilatation balloon catheter.

2. Description of the Prior Art

Angioplasty has gained wide acceptance in recent years as an efficient and effective method for opening stenoses in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation to the balloon causes stretching of the artery and pressing of the lesion into the artery wall to re-establish acceptable blood flow through the artery.

One important characteristic of a dilatation balloon catheter used for angioplasty is its "profile", which is determined by the outer diameter of the distal end portion of the balloon. Considerable effort has been spent in developing low profile dilatation balloon catheters by minimizing the dimensions of the core or inner tube which extends through the balloon to its distal end, and by reducing wall thicknesses, to the extent possible, of the balloon itself.

Another important consideration is the outer diameter of the balloon in its deflated condition. This outer diameter affects the ease and ability of the dilatation catheter to pass through a guide catheter and through the coronary arteries leading to the stenosis to be opened.

In order to reduce the outer diameter of the balloon catheter in its deflated condition, it is common to fold and/or wrap the flaps of the deflated balloon. When inflation fluid is applied to the deflated balloon, it causes the balloon flaps to unwrap so that the balloon can inflate to its full inflated state.

It has been common to use a balloon protector in conjunction with a balloon dilatation catheter. A balloon protector serves two important functions. First, it protects the balloon and the distal tip of the catheter from possible damage during shipping. Second, the balloon protector wraps the balloon tightly in its deflated condition to minimize the outer diameter of the balloon in its deflated state.

A balloon protector is typically applied to the distal end portion of the catheter prior to sterilization of the catheter. The sterilization process typically involves exposing the catheter, with the balloon protector in place, to an elevated temperature for a predetermined time period.

With certain balloon materials, such as polyolefin, the sterilization process will cause the balloon to be "heat set" in the folded or wrapped condition in which it is held by the balloon protector. As a result, when the balloon protector is later removed, the balloon remains in a tightly wrapped condition. This heat set of balloon has a further advantage in that when the balloon is inflated and is then deflated, the application of a negative fluid pressure during deflation will cause the balloon to tend to return to its heat set, tightly-wrapped shape. This greatly facilitates the removal of the catheter after the dilatation procedure has been performed.

As the catheter distal sections (including the balloon) have become smaller, and more fragile, it has become increasing difficult to apply a balloon protector which does not damage the catheter or the balloon and yet wraps the balloon as tightly as possible. There is a continuing need for improved balloon protectors for dilatation balloon catheters.

SUMMARY OF THE INVENTION

The present invention is a balloon protector for covering the balloon of a dilatation catheter which makes use of a first protector which is positioned over a first segment of the balloon and a second protector which is positioned over a second segment of the balloon. By using several protectors, each of which tightly fits over a part of the balloon, the force required to apply each protector individually is significantly less than the force required to apply a tightly-fitting balloon protector which extends over the entire length. This reduces the chances of damaging the balloon during application of the balloon protector.

DETAILED DESCRIPTION OF THE PREFERRED EMBODIMENTS

Figure 1A:
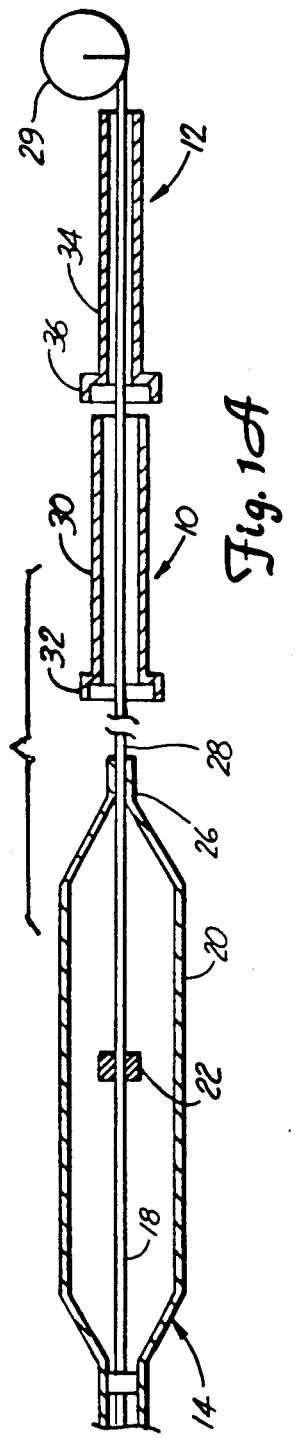
FIGS. 1A-1D illustrate the application of a preferred embodiment of the multisegment balloon protector of the present invention to a dilatation balloon catheter.

In FIGS. 1A-1D, a multisegment balloon protector formed by proximal balloon protector 10 and distal balloon protector 12 is applied to a distal portion of dilatation balloon catheter 14. In the particular embodiment shown in FIGS. 1A-1D, catheter 14 is an "over-the-wire" type of multilumen dilatation catheter.

Catheter 14 includes outer tube 16, inner tube 18, balloon 20 and radiopaque mid-balloon marker 22. Inner tube 18 extends through outer tube 16 and defines a guide wire lumen or thru lumen which extends the entire length of catheter 14. The space between inner tube 18 and outer tube 16 defines an inflation lumen through which an inflation fluid is supplied under pressure to inflate balloon 20. As is well known in the art, the proximal ends of tubes 16 and 18 are attached to a manifold (not shown) which in turn is be connected to an inflation device.

Balloon 20 has its proximal end attached to outer tube 16 at proximal bond location 24. The distal end of balloon 20 is bonded to inner tube 18 at distal bond location 26.

As illustrated in FIG. 1A, the application of the balloon protector of the present invention begins with the insertion of product mandrel 28 into the distal end of inner tube 18. Mandrel 28, which is preferably a metal wire with a loop or handle 29 at one end, provides support for the distal portion of catheter 14 during the application of balloon protectors 10 and 12.

Proximal balloon protector 10 and distal balloon protector 12 are carried on mandrel 28 with proximal balloon protector 10 being located closer to balloon 20 than is distal balloon protector 12.

Proximal balloon protector 10 includes a main tubular or sleeve region 30 and a proximal step or socket region 32. Step region 32 has a larger inner and outer diameter than main sleeve region 30. The inner diameter of sleeve region 30 will define the outer diameter of the proximal half of balloon 20 when balloon protector 10 is in place.

Distal balloon protector 12 has a main sleeve region 34 and a proximal step or socket region 36. The inner diameter of step 36 is sized to mate with the outer diameter of the distal end portion of sleeve region 30 of proximal balloon protector 10. This allows proximal and distal balloon protectors 12 to be joined together (as illustrated in FIG. 1D).

Figure 1B:

In FIG. 1B, a vacuum has been applied to the inflation lumen of catheter 14 by the inflation device (not shown). This causes balloon 20 to collapse into a deflated condition. As balloon 20 is collapsed, it is wrapped around inner tube 18 to reduce the overall outer diameter of the distal portion of catheter 14.

Figure 1C:
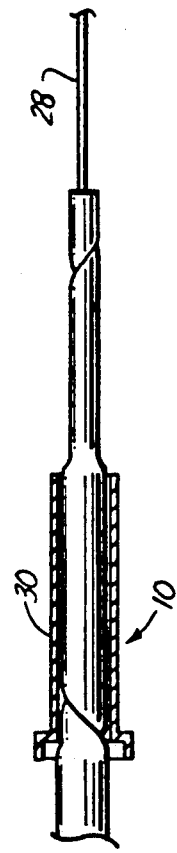

In FIG. 1C, proximal balloon protector 10 has been applied over the proximal half of balloon 20. Proximal balloon protector 10 is moved in the proximal direction over mandrel 28 and over balloon 20 until step 32 is generally aligned with proximal bond region 24. This leaves the distal end of balloon protector 10 aligned generally with mid-balloon marker 22.

Figure 1D:
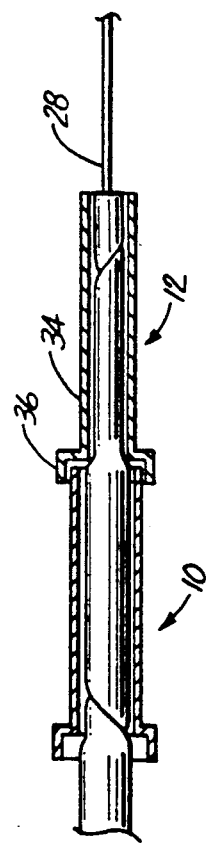

Next, distal balloon protector 12 is applied over balloon 20 until proximal end 36 of balloon protector 12 is positioned over distal end 30 of balloon protector 10 as shown in FIG. 1D. This joint between balloon protectors 10 and 12 allows both protectors 10 and 12 to be removed together by pushing distally on proximal balloon protector 10. In addition, the entire length of balloon 20 is held generally rigid (i.e. no flexing at the joint) during shipping and handling.

The inner diameter of main sleeve region 34 of balloon protector 12 is preferably smaller than the inner diameter of sleeve region 30 of proximal balloon protector 10. This is because it is desireable to minimize the outer diameter of balloon 10 from mid-balloon marker 22 to the distal end of catheter 14.

Balloon protectors 10 and 12 are preferably of a polymeric material, such as a heat shrinkable polytetrafluorethylene. The inner surfaces of balloon protectors 10 and 12 must exhibit low surface friction characteristics to facilitate the application of balloon protectors 10 and 12 over the balloon and by sliding.

The heat shrinkable characteristic of balloon protectors 10 and 12 allows the balloon protector of the present invention to further reduce the outer diameter of balloon 20 during the sterilization process. This sterilization process is preferably performed with the balloon protectors 10 and 12 in place over balloon 10. Sterilization is performed at an elevated temperature.

Figure 2:
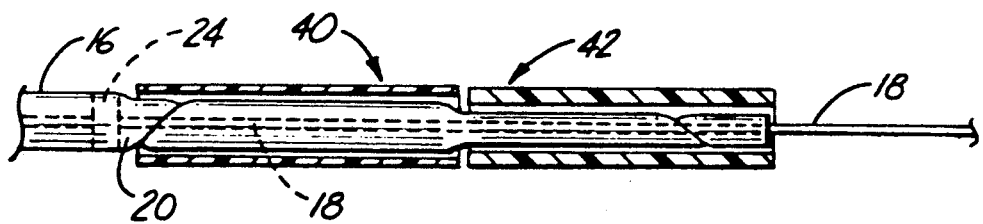
FIG. 2 shows a view, partially in section, of a dilatation balloon catheter with another embodiment of the multisegment balloon protector of the present invention.
Figure 3:
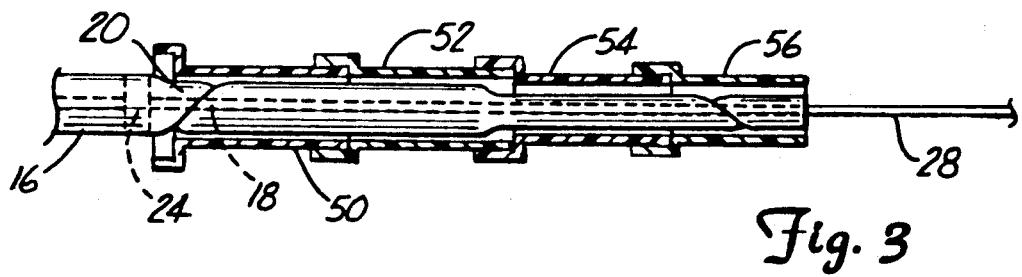
FIG. 3 shows the embodiment of the multisegment balloon protector of the present invention applied to a dilatation balloon catheter, which includes four balloon protectors connected together serially.
Figure 4:
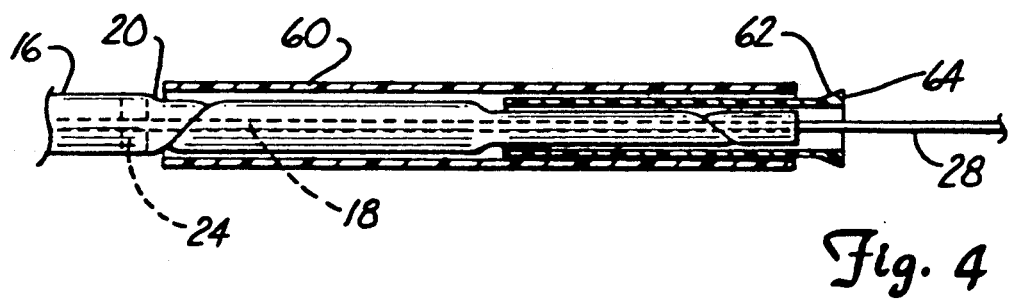
FIG. 4 shows another embodiment of the multisegment balloon protector of the present invention, applied to a dilatation balloon catheter in which balloon protector includes a full length proximal balloon protector and a half length distal balloon protector which fits within the proximal balloon protector.

FIGS. 2, 3 and 4 show other embodiments of the multisegment balloon protector of the present invention. In FIG. 2, the multisegment balloon protector includes proximal balloon protector 40 and distal balloon protector 42 which are tubes having the same outer diameter but different inner diameters. In particular, the wall thickness of the tube forming distal balloon protector 42 is greater than the wall thickness of the tube forming proximal balloon protector 40, so that the inner diameter of balloon protector 42 is smaller.

In FIG. 3, the multisegment balloon protector is formed by four balloon protectors 50, 52, 54, and 56, which are generally similar in shape to balloon protectors 10 and 12 shown in FIGS. 1A-1D Any multiple linear combination of balloon protector segments is possible. As shown in FIG. 3 each of the segments can be made to interlock with an adjacent balloon protector segment so that the entire length of balloon 20 is maintained generally rigid during shipping and handling. In the particular embodiment shown in FIG. 3, the inner diameters of balloon protectors 54 and 56 (which cover the distal half of balloon 20) are smaller than the inner diameters of the more proximal balloon protectors 50 and 52.

FIG. 4 shows a configuration in which proximal balloon protector 60 is a sleeve which slides freely over the distal half of balloon 20 and which covers essentially the entire length of balloon 20. Distal protector 62 is then inserted into the distal end of proximal balloon protector 60 so that it is positioned between protector 60 and the distal half of balloon 20. In the embodiment shown in FIG. 4, a flange 64 is provided at the distal end of balloon protector 62 to facilitate insertion and removal of balloon protector 62 from within balloon protector 60.

In conclusion, with the multisegment balloon protectors of the present invention, far less force is required to apply the protectors over the balloon than is required when a single full length protector is used because each segment of the balloon protector of the present invention is applied separately. This minimizes the danger of damages to the balloon as balloon protectors are applied while ensuring close tolerances between the deflated balloon and the balloon protector.

Although the present invention has been described with reference to preferred embodiments, workers skilled in the art will recognize that changes may be made in form and detail without departing from the spirit and scope of the invention.

What is claimed:

1. A method of covering a deflated balloon positioned adjacent a distal end of a balloon catheter, the method comprising:
   positioning a first protector over a first expandable segment of the deflated balloon; and
   positioning a second protector over a second expandable segment of the deflated balloon, the second segment being located distally of the first segment.

2. The method of claim 1 wherein the first protector has a first inner diameter, and the second protector has a second, smaller inner diameter.

3. The method of claim 1 and further comprising:
   connecting together the first and second protectors in end-to-end relationship.

4. The method of claim 3 wherein the connecting is provided by:
   a male connector carried by one of the first and second protectors; and a female connector carried by the other protector.

5. The method of claim 4 wherein the male connector is located at a distal end of the first protector and the female connector is located at a proximal end of the second protector.

6. The method of claim 1 wherein the first and second protectors are formed of polytetrafluorethylene.

7. The method of claim 1 and further comprising:
positioning a third protector over a third expandable segment of the balloon which is located distally of the second segment.

8. The method of claim 1 wherein the first and second protectors are first and second tube sections, respectively.

9. The method of claim 8 wherein the first, and second tube sections have approximately equal outer diameters, and wherein the second tube section has an inner diameter which is less than an inner diameter of the first tube section.

10. The method of claim 8 wherein the first tube section is longer than the second tube section and wherein the second tube section has an outer diameter which is less than an inner diameter of the first tube section.

11. The method of claim 10 wherein the first tube section has a length approximately equal to a length of the balloon.

12. The method of claim 10 wherein the second tube section has a outwardly projecting lip at a distal end.

13. The method of claim 1 wherein the second protector has a portion which is adapted to extend into a distal end portion of the first protector.

14. In combination:
a balloon catheter having a shaft and a deflated balloon attached to the shaft at a distal end of the shaft; and
a multipart balloon protector covering the deflated balloon, the balloon protector comprising:
a first protector covering a first expandable segment of the balloon; and
a second protector covering a second expandable segment of the balloon, wherein the second segment of the balloon is located distally of the first segment.

15. The combination of claim 14 wherein the first protector has a first inner diameter, and the second protector has a second, smaller inner diameter.

16. The combination of claim 14 wherein the first and second protectors are connected together in end-to-end relationship.

17. The combination of claim 16 wherein the second protector has a female connector portion at a proximal end into which a distal end of the first protector is inserted.

18. The combination of claim 14 wherein the balloon protector further comprises:
a third protector covering a third expandable segment of the balloon.

19. The combination of claim 14, wherein the first and second protectors are first and second tube sections, respectively.

20. The combination of claim 19 wherein the first and second tube sections have approximately equal outer diameters, and wherein the second tube section has an inner diameter which is less than an inner diameter of the first tube section.

21. The combination of claim 19 wherein the first tube section has a length approximately equal to a length of the balloon and wherein the second tube section is shorter than the first tube section and has a portion which is positioned within the first tube section.

22. The combination of claim 21 wherein the second tube section has an outwardly projecting lip at a distal end.

23. In combination:
an angioplasty dilation balloon catheter having a shaft with an inflatable balloon at a distal end of the shaft, the balloon being deflated and wrapped about a core which extends through the balloon;
a first balloon protector covering a proximal expandable portion of the balloon, the first balloon protector having a first inner diameter; and
a second balloon protector covering a distal expandable portion of the balloon, the second balloon protector having a second, smaller inner diameter.

24. The combination of claim 23 wherein the first and second balloon protectors are connected together in end-to-end relationship.

25. The combination of claim 23 wherein the second balloon protector has a female connector portion at a proximal end into which a distal end of the first balloon protector is inserted.

26. The combination of claim 23, wherein the first and second balloon protectors are first and second tube sections, respectively.

27. The combination of claim 23 wherein the first and second tube sections have approximately equal outer diameters, and wherein the second tube section has an inner diameter which is less than an inner diameter of the first tube section.

28. The combination of claim 23 wherein the first tube section has a length approximately equal to a length of the balloon and wherein the second tube section is shorter than the first tube section and has a portion which is positioned within the first tube section.

29. The combination of claim 23 wherein the second tube section has an outwardly projecting lip at a distal end.

30. In combination:
an angioplasty dilation balloon catheter having a shaft with an inflatable balloon at a distal end of the shaft, the balloon being deflated and wrapped about a core which extends through the balloon; and
a multisegment balloon protector formed by a plurality of separable tubular members each of which covers and tightly fits over a different expandable portion of the deflated balloon.

* * * * *